(12) United States Patent
Vanderpool

(10) Patent No.: US 9,572,970 B2
(45) Date of Patent: Feb. 21, 2017

(54) TRANSCUTANEOUS IMPLANT TOOLS, SYSTEMS AND METHODS

(75) Inventor: Matthew T. Vanderpool, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1059 days.

(21) Appl. No.: 13/487,284

(22) Filed: Jun. 4, 2012

(65) Prior Publication Data

US 2013/0324977 A1 Dec. 5, 2013

(51) Int. Cl.
*A61B 17/00* (2006.01)
*A61M 31/00* (2006.01)
*A61M 37/00* (2006.01)

(52) U.S. Cl.
CPC ..... *A61M 37/0069* (2013.01); *A61B 2560/063* (2013.01)

(58) Field of Classification Search
CPC ............. A61M 31/007; A61M 37/0069; A61B 2560/063
See application file for complete search history.

(56) References Cited

U.S. PATENT DOCUMENTS

| | | | |
|---|---|---|---|
| 4,900,304 A * | 2/1990 | Fujioka et al. ................. | 604/60 |
| 5,520,660 A | 5/1996 | Loos et al. | |
| 5,772,671 A | 6/1998 | Harmon | |
| 5,987,352 A | 11/1999 | Klein et al. | |
| 6,190,350 B1 | 2/2001 | Davis et al. | |
| 6,230,059 B1 | 5/2001 | Duffin | |
| 6,436,068 B1 | 8/2002 | Bardy | |
| 7,736,330 B2 | 6/2010 | Bardy | |
| 2007/0078397 A1 | 4/2007 | Weststrate | |
| 2010/0331868 A1 | 12/2010 | Bardy | |
| 2010/0331874 A1* | 12/2010 | Bardy .......................... | 606/185 |
| 2011/0144440 A1 | 6/2011 | Cropper et al. | |

FOREIGN PATENT DOCUMENTS

| | | | |
|---|---|---|---|
| CN | 101111279 A | | 1/2008 |
| CN | 102039001 A | | 5/2011 |
| EP | 2 078 535 | * | 7/2009 |
| EP | 2078535 A1 | | 7/2009 |
| GB | 2346329 | | 8/2000 |

OTHER PUBLICATIONS

Lee et al., "Percutaneous Delivery Tool", filed May 5, 2011, U.S. Appl. No. 13/101,613, 42 pages.
(PCT 2013/035875) PCT Notification of Transmittal of the International Search Report and the Written Opinion of the International Searching Authority, Mailed Jul. 9, 2013, 10 pages.
Office Action mailed Jul. 7, 2016, 5 pages, English translation.
Office Action mailed Jul. 7, 2016, 5 pages, Chinese language.

* cited by examiner

*Primary Examiner* — Matthew F DeSanto
(74) *Attorney, Agent, or Firm* — Scott A. Bardell

(57) ABSTRACT

A transcutaneous implant tool is used to push a medical element through an incision and into a patient's subcutaneous tissue, while a fin of the tool is engaged beneath the patient's skin at the incision site. The tool preferably includes an injection rod for moving the medical element out through an opening of a bore of the tool. The fin, which is located in proximity to the opening, preferably includes a distal-facing surface that extends proximally from the opening at an acute angle with respect to a longitudinal axis of the bore; and the injection rod preferably includes a distal surface that is approximately coplanar with the distal-facing surface of the fin, when the distal surface of the rod is located in proximity to the opening of the bore.

22 Claims, 6 Drawing Sheets

TRANSCUTANEOUS IMPLANT TOOLS, SYSTEMS AND METHODS

FIELD OF THE DISCLOSURE

The present invention pertains to medical implants, and, more particularly to transcutaneous tools, systems and methods for medical implants.

BACKGROUND

Various types of medical elements that are designed for implant within a patient's subcutaneous tissue are known in the art, for example, electronic sensors/monitors and/or transmitters and drug delivery devices. Many of these medical elements have been miniaturized so that they may be inserted transcutaneously into the subcutaneous tissue, for example, using a tool patterned after a needle-tipped injection syringe. A variety of such tools are known in the art, but there is still a need for new configurations of transcutaneous implant tools and associated implant methods that are ergonomic and can increase a positional stability of the implanted medical element.

SUMMARY

According to preferred methods of the present invention, a transcutaneous implant tool is used to push a medical element through an incision and into a patient's subcutaneous tissue, while a fin of the tool is engaged beneath the patient's skin at the incision site. The transcutaneous implant tool, according to some embodiments and methods of the present invention, includes an injection rod that can be moved within a bore defined by a body of the tool, to push the medical element out from the bore, through an opening thereof, and into the patient's subcutaneous tissue, while the fin of the implant tool, which is connected to the body in proximity to the opening of the bore, is engaged beneath the patient's skin at an incision site. According to preferred embodiments, the fin of the implant tool includes a distal-facing surface that extends proximally from the opening of the bore at an acute angle with respect to a longitudinal axis of the bore; and the injection rod of the implant tool preferably includes a distal surface that is approximately coplanar with the distal-facing surface of the fin, when the distal surface of the rod is located in proximity to the opening of the bore.

Some systems of the present invention preferably include an implant tool, like that described above, in which a medical element is pre-loaded, such that the medical element is wholly contained within the bore prior to moving the injection rod toward the opening of the bore. According to some preferred embodiments, a perimeter profile of the bore approximately matches that of the medical element contained therein. The medical element may include a therapeutic and/or diagnostic component, such as a drug, a transmitter, an electrode, or any other suitable type of sensor.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives. Examples of constructions, materials, dimensions and fabrication processes are provided for select elements and all other elements employ that which is known by those skilled in the art.

Figure 2:
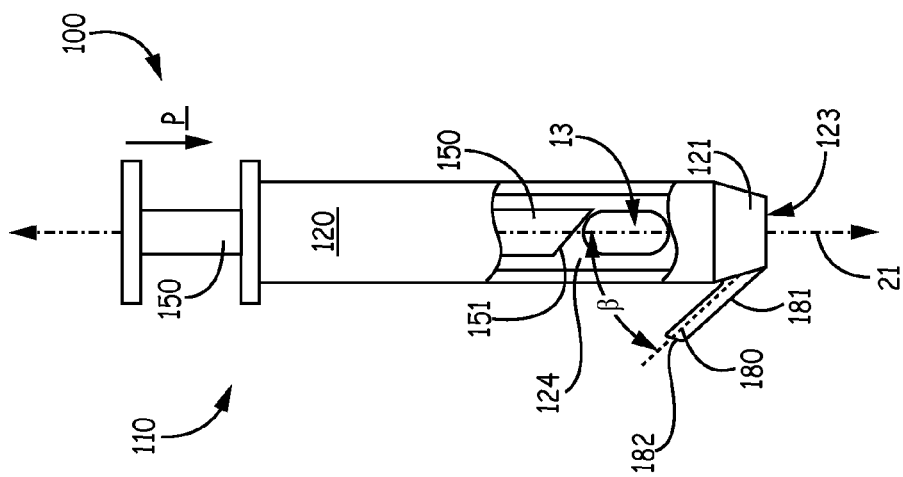
FIG. 2 is a plan view, with partial section, of a medical system, according to some embodiments of the present invention.
Figure 1:
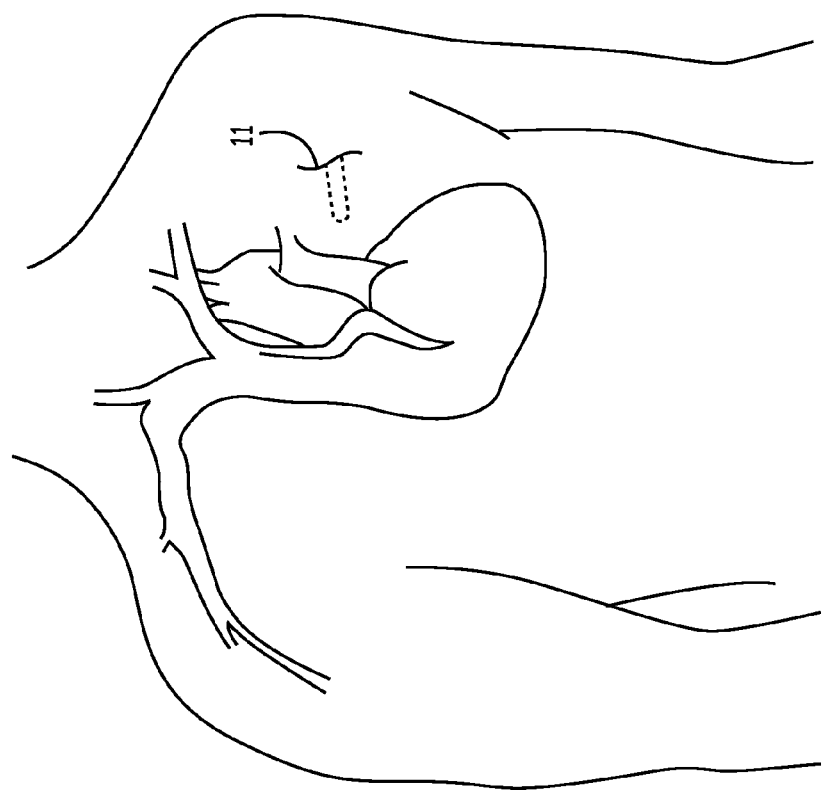
FIG. 1 is a schematic of a patient's pectoral region, which may be a location for a subcutaneous implant, according to some methods of the present invention.

FIG. 1 is a schematic of a patient's pectoral region, which may be a location for a subcutaneous implant, according to some methods of the present invention. FIG. 1 illustrates an incision 11, for example, formed by a scalpel cut, through which a medical element (shown with dotted lines) has been implanted into subcutaneous tissue. The medical element may be an electronic cardiac monitoring device that functions similarly to embodiments described in commonly-assigned U.S. Pat. Nos. 5,987,352 and 6,230,059, and in co-pending and commonly-assigned patent application Ser. No. 13/101,613, for example, a miniature configuration of the Reveal® device manufactured by Medtronic, Inc. of Minneapolis, Mn. According to some embodiments of the present invention, a medical element, such as medical element 13 of FIG. 2, is part of a medical system 100. It should be noted that other incision sites for implant locations, for example, in an arm or abdomen, may be more suitable for alternate embodiments of medical systems that include different types of medical elements, for example, other types of sensing and/or transmitting implants or drug delivery implants.

FIG. 2 is a plan view, with partial section, of medical system 100, which includes medical element 13 pre-loaded within a subcutaneous implant tool 110 of system 100. FIG. 2 illustrates tool 110 including an elongate body 120 defining a bore 124 in which medical element 13 is contained. According to the illustrated embodiment, an injection rod 150, which fits within bore 124, may be moved, per arrow P, to push medical element 13 out from an opening 123 of bore 124, which opening 123 is formed at a distal end 121 of body 120. FIG. 2 further illustrates tool 110 including a fin 180, which is connected to body 120 in proximity to distal end 121, and which has a distal-facing surface 181 that extends proximally to a terminal end 182 of fin 180 at an acute angle β, with respect to a longitudinal axis 21 of bore 124. Angle β is no greater than approximately 60 degrees, and preferably between approximately 30 degrees and approximately 45 degrees.

Figure 3A:
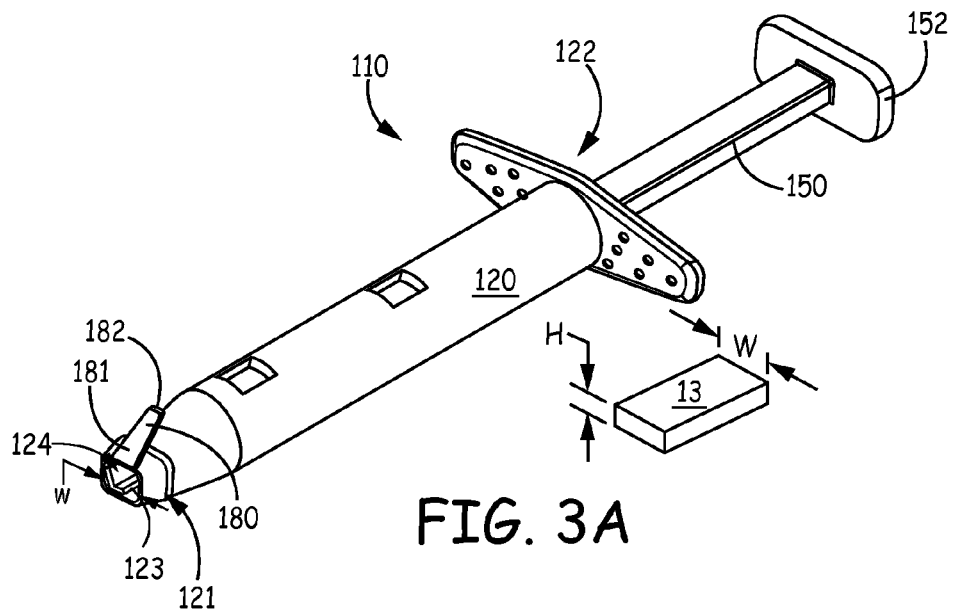
FIG. 3A is a perspective view of a transcutaneous implant tool alongside a medical element, according to some embodiments.
Figure 3B:
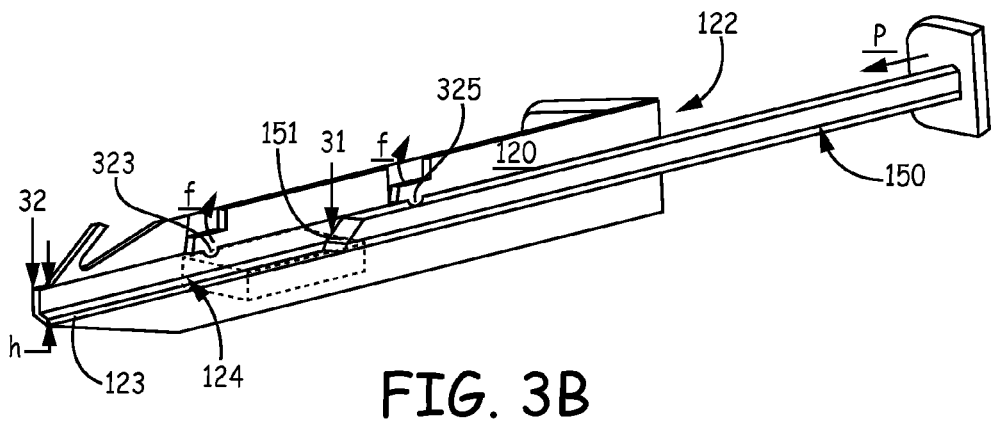
FIG. 3B is a perspective view, axial cross-section view of the implant tool, according to some embodiments.

FIG. 3A is a perspective view of transcutaneous implant tool 110 alongside medical element 13, according to some embodiments; and FIG. 3B is an axial cross-section view of implant tool 110. FIGS. 3A-B illustrate bore 124 and injection rod 150 each having a perimeter profile that approximately matches that of medical element 13, according to preferred embodiments, for example, to maintain a positional stability of injection rod 150 and medical element 13 within bore 124, as rod 150 moves within bore 124, to push medical element 13 out from opening 123. According to some exemplary embodiments, a width w of bore 124 is between approximately 0.7 and one cm, and a height h of bore is between approximately 0.4 and 0.5 cm, each of which is only slightly larger, i.e. on the order of 0.025 mm, than the corresponding height H and width W of medical element 13.

FIG. 3B further illustrates a distal surface 151 of rod 150 located at a first position 31 within bore 124, such that there is a sufficient length of bore 124 to contain medical element 13 (shown with phantom lines), prior to moving distal surface 151 of injection rod 150, per arrow P, to a second position 32, at which medical element 13 is pushed out from distal opening 123 of bore 124. With further reference to FIGS. 2 and 3B, distal surface 151 of rod 150 extends at an angle with respect to axis 21, which angle is approximately equal to acute angle β of distal-facing surface 181 of fin 180, such that, when distal surface 151 is located at second position 32, distal surface 151 is approximately coplanar with distal-facing surface 181 of fin 180, for example, as illustrated in FIG. 4C. According to some exemplary embodiments, a distance between first position 31 and second position 32 is between approximately 4 cm and 6 cm.

Figure 4:
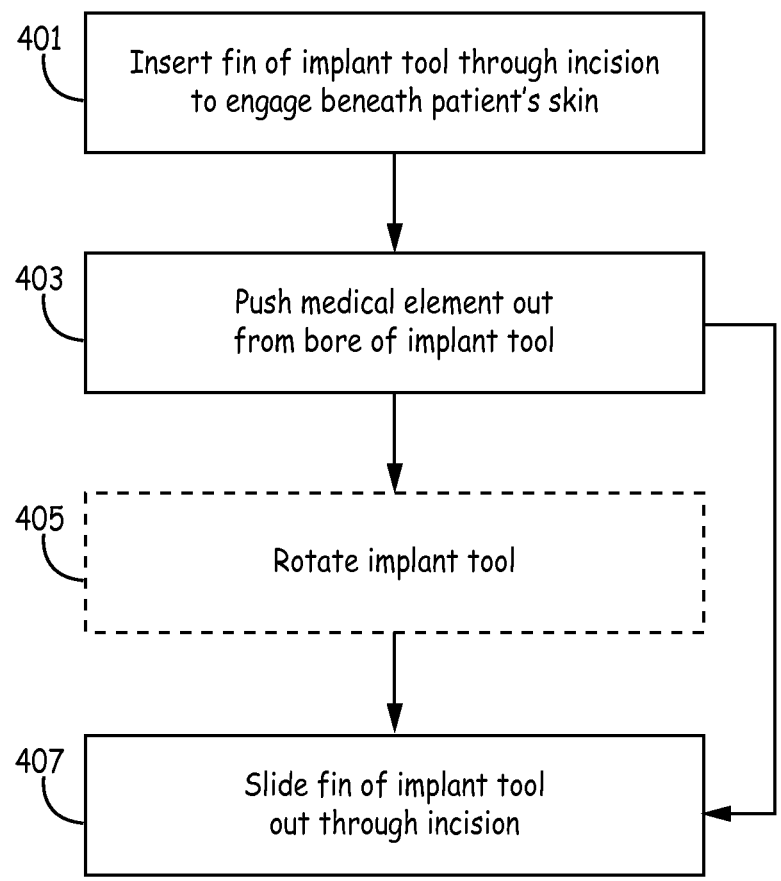
FIG. 4 is a flow chart outlining some methods of the present invention.
Figures 4A, 4B:
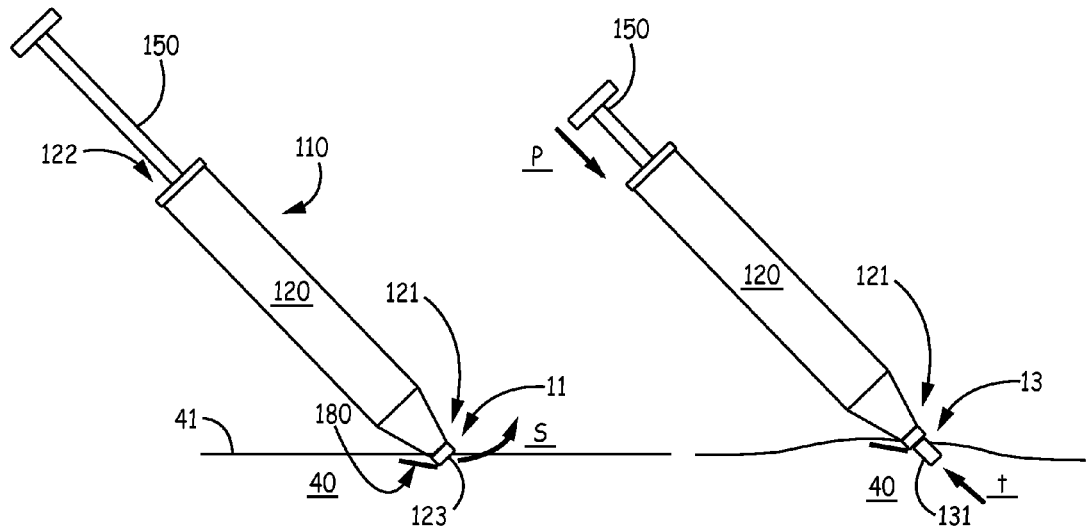
FIGS. 4A-D make up a series of schematics, for reference in conjunction with the flow chart of FIG. 4.
Figures 4C, 4D:
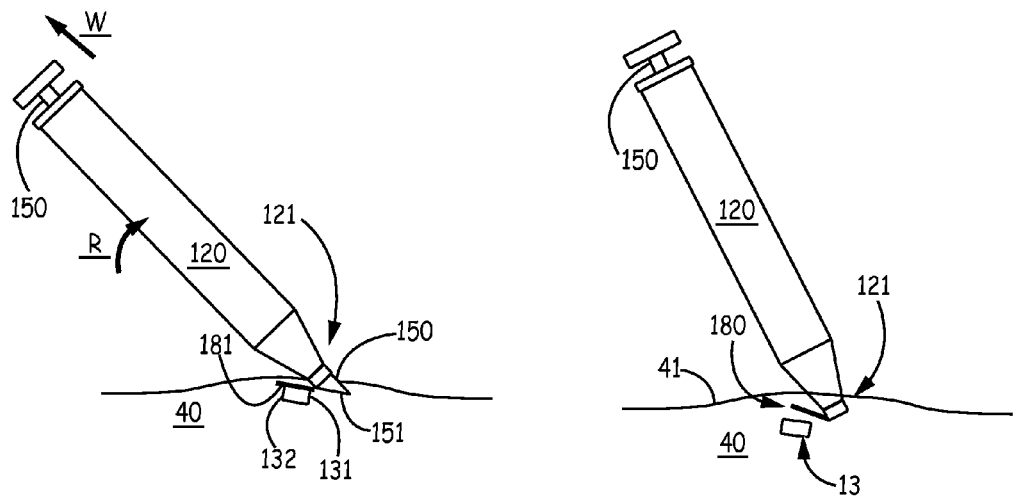

FIGS. 4A-D are schematics, for reference in conjunction with a flow chart shown in FIG. 4, which outlines steps of some methods of the present invention.

The methods are described in conjunction with implant tool 110, but it should be noted that any of the other embodiments of implant tools, which are described below, may be similarly employed. With reference to FIG. 4, according to step 401, fin 180 of implant tool 110 is inserted through incision 11, for example, as illustrated in FIG. 4A, to engage fin 180 beneath a patient's skin 41 at the incision site, such that opening 123 of bore 124 is located between opposing edges of incision 11. Engagement of fin 180 can help to stabilize tool 110 for the subsequent step 403 of pushing medical element 13 out from bore 124, for example, as illustrated in FIGS. 4B-C.

With reference back to FIG. 3B, body 120 of transcutaneous implant tool 110 preferably includes retention features 323, 325 for temporarily holding medical element 13 and injection rod 150, respectively, in their initial positions, for example, when system 100 is removed from a sterile package and positioned for insertion of fin 180 through incision 11. According to the illustrated embodiment each of feature 323, 325 is formed as a detent in a wall of body 120 of implant tool 110, such that friction forces between feature 323 and element 13 and between feature 325 and rod 150, within bore 124, retain element 13 and rod 150, until a force of rod 150 moving, per arrow P, overcomes the friction forces. FIG. 3B further illustrates each feature 323, 325 formed on a cantilevered segment that can flex outward, for example, per arrow f, to prevent binding of element 13 and rod 150 within bore 124. It should be noted that, according to alternate embodiments, only one of retention features 323, 325 is included in tool 110. For example, according to some alternate embodiments, injection rod 150 need not be positioned in bore 124 when fin 180 is inserted through incision 11, but inserted into bore 124 at a proximal opening thereof, for example, located at a proximal end of body 122, after engagement of fin 180 stabilizes tool 110.

In FIG. 4B, injection rod 150 has been moved, per arrow P, so that a distal end 131 of medical element 13 protrudes out from distal opening 123 of bore 124 and into subcutaneous tissue 40. Arrow t in FIG. 4B denotes an opposing force, which is applied by stored energy in the viscoelastic subcutaneous tissue against distal end 13, as rod 150 continues to push, per arrow P. Once an entirety of element 13 is pushed out from bore 124, as shown in FIG. 4C, the position of distal surface 151 of rod 150 (i.e. second position 32 of FIG. 3B), approximately coplanar with distal-facing surface 181 of inserted fin 180, allows distal surface 151 and distal-facing surface 181 to form a kind of ramp, for orienting and guiding, along which the aforementioned opposing force of the subcutaneous tissue 40 moves medical element 13 into a stable subcutaneous position, for example, at a depth of approximately one cm below skin 41. With reference to FIG. 4C, it may be appreciated that a proximal end 132 of element 13 slides back along distal surface 151 and distal-facing surface 181 in response to the force per arrow t, once an entirety of element 13 is outside of bore 124.

Once injection rod 150 has pushed medical element 13 out from bore 124, rod 150 is preferably withdrawn into bore 124, per arrow W of FIG. 4C, prior to sliding fin 180 out through incision 11, per step 407 of FIG. 4, for example, according to arrow S shown in FIG. 4A. According to some embodiments, injection rod 150 may be spring loaded to automatically withdraw distal surface 151 thereof back into bore 124 when the push force, per arrow P, is removed. The resulting subcutaneous implant of medical element 13 is stable by virtue of a relatively snug fit of element 13 within tissue 40, and by virtue of a location, beneath the area where fin 180 was engaged, which is laterally offset from the edges of incision 11. According to some alternate methods, prior to sliding fin 180 out through incision 11, implant tool 110 can be rotated in the direction of arrow R (FIG. 4C), per optional step 405 of FIG. 4, so that fin 180 stretches skin 41 and applies an additional force against element 13 to push element 13 a bit farther away from the edges of incision 11, for example, as illustrated in FIG. 4D. According to some embodiments, fin 180 may flex a bit with respect to body 120, to prevent inordinate trauma at incision 11 when tool 110 is rotated per arrow R.

Figure 5A:
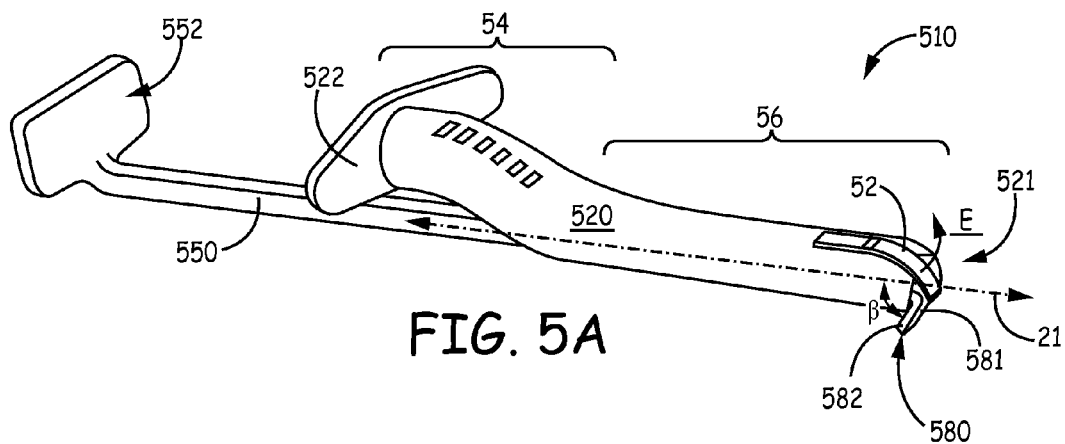
FIGS. 5A-B are perspective views (5B in axial cross-section) of a transcutaneous implant tool, according to some alternate embodiments.
Figure 5B:
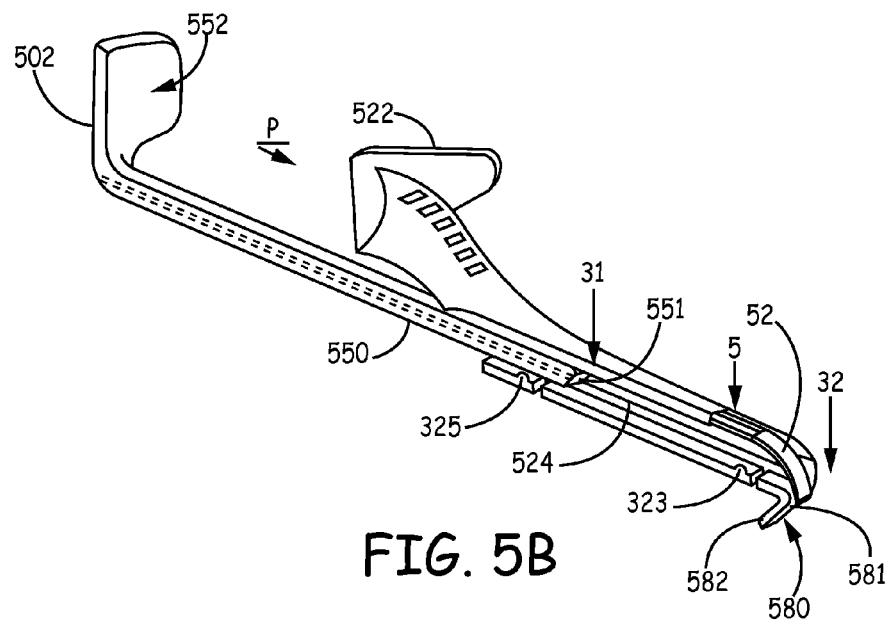

FIGS. 5A-B are perspective views (5B in axial cross-section) of a transcutaneous implant tool 510, according to some alternate embodiments, wherein a body 520 of tool 510 includes a proximal section 54 and a distal section 56; and wherein a bore 524, which extends through distal section 56 of body 520, and along longitudinal axis 21, has an opening defined by an expandable portion 52 of a distal end 521 of body 520. FIGS. 5A-B illustrate tool 510, like tool 110, including a fin 580, which is connected to body 520 in proximity to distal end 521, and an injection rod 550 that fits within bore 524; a distal-facing surface 581 of fin 580 is shown extending proximally to a terminal end 582 of fin 580 at the acute angle β, with respect to longitudinal axis 21 of bore 524, and a distal surface 551 of rod 550 is shown extending at a similar angle. According to the illustrated embodiment, distal end 521 may be inserted between opposing edges of an incision, i.e. incision 11, alongside fin 580, and, as injection rod 550 is moved, per arrow P, for example, from first position 31 toward second position 32, to push a medical element, i.e. element 13, through distal end 521, expandable portion 52 is forced outward, per arrow E, to spread apart the opposing edges of the incision and to define an opening of bore 524 at distal end 521, through which the medical element is further pushed by rod 550 out into subcutaneous tissue, until distal surface 551 of rod 550 is approximately coplanar with distal-facing surface 581 of fin 580. FIG. 5B further illustrates injection rod 550 including an optional lumen (shown with dashed lines) extending from a proximal opening, at a proximal-facing surface 502 of a lateral projection 552, to a distal opening at distal surface 551. Such a lumen may be included in other embodiments of tools illustrated herein, and may be useful for the injection of a lubricating fluid into bore 524 to facilitate in pushing the medical element out from bore 524, or for holding a tether to temporarily secure a medical element within bore 524, for example, if retention feature 323 is not included.

With further reference to FIGS. 5A-B, proximal section 54 of body 520 of tool 510 extends laterally away from longitudinal axis 21 and proximally from distal portion 56 to a proximal end 522 of body 520. According to the illustrated embodiment, lateral projection 552 of injection rod 550, which is located at a proximal end of rod 550, outside bore 524, will abut proximal end 522 of body 520 when distal face 551 of rod 550 is moved past second position 32. The lateral extension of proximal section 54 of body 520, in conjunction with lateral projection 552, may provide a more ergonomic orientation of tool 510 within a hand of an implanting clinician whose forefinger and adjacent finger are engaged with surfaces of proximal end 522, on either side of body 520, and whose pad of the hand, adjacent to the thumb, is engaged against proximal-facing surface 502 of rod 550, to insert fin 580 and then to push rod 550, per arrow P.

Figure 6:
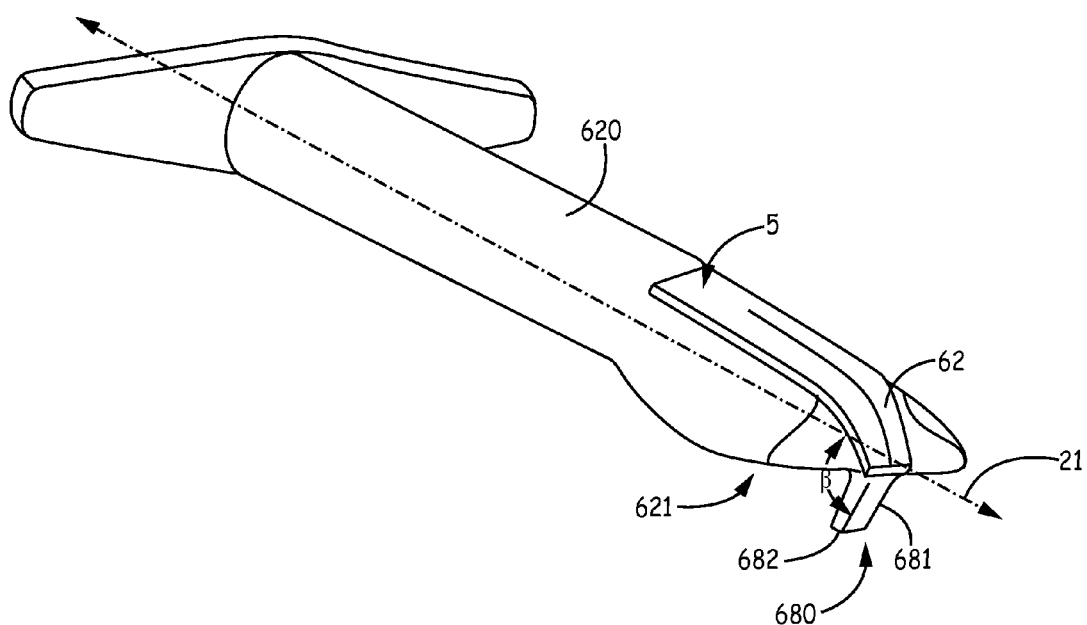
FIG. 6 is a perspective view of a body of another transcutaneous implant tool, according to yet further embodiments.

FIG. 6 is a perspective view of an elongate body 620 of another transcutaneous implant tool, according to yet further embodiments. FIG. 6 illustrates a fin 680 connected to a distal end 621 of body 620, wherein fin 680, like fins 180 and 580 of the above-described embodiments, includes a distal-facing surface 681 that extends proximally at the acute angle R, with respect to longitudinal axis 21. Although not shown, it should be understood that body 620 defines a bore, which extends along longitudinal axis 21, and in which an injection rod may be inserted, and in which a medical element may be contained, as described above for tools 110 and 510. FIG. 6 further illustrates distal end 621 being enlarged from an adjacent section of body 620, and enlarged distal end 621 including an expandable portion 62, similar to expandable portion 52 of tool 510, which defines an opening of the bore of tool 610, when expanded. According to the illustrated embodiment, enlarged distal end 621 can prevent the implanting physician from engaging fin 680 too deeply beneath a patient's skin, which might harm the patient and/or make fin 680 too difficult to remove upon completion of the implant.

Parts of each of the embodiments of implant tools 110, 510, 610 described herein are preferably wholly formed from one or more medical grade plastics, for example, polycarbonate, polypropylene, and/or nylon, which are injection molded according to methods known in the art. Each of fins 180, 580, 680 may be integrally formed with the corresponding body 120, 520, 620, or formed as a separate part that is attached to the corresponding body, for example, by insert molding or bonding methods known in the art. In order to increase an ease of insertion beneath the skin, each of fins 180, 580, 680 preferably taper inward across a width of the corresponding distal-facing surface 181, 581, 681 and toward the corresponding terminal end 182, 582, 682, as can be seen for fin 180 in FIG. 3A. Furthermore, edges of fins 180, 580, 680 are preferably rounded to minimize trauma during the implant procedure and a junction of each fin with the corresponding body may be somewhat flexible, as previously described in conjunction with FIGS. 4C-D. With reference back to implant tool bodies 520, 620, shown in FIGS. 5A-B and 6, respectively, expandable portions 52, 62 of corresponding distal ends 521, 621 are preferably integrally formed flaps that flex to expand around a living hinge feature, for example, at the general location of reference numeral 5. However, according to some alternate embodiments, expandable portions 52, 62 may be separately formed and then attached to bodies 521, 621, for example, by mechanical interlocking at a hinged joint.

In the foregoing detailed description, the invention has been described with reference to specific embodiments. However, it may be appreciated that various modifications and changes can be made without departing from the scope of the invention as set forth in the appended claims.

The invention claimed is:

1. A transcutaneous implant tool comprising:
    an elongate body defining a bore and having a length along which the bore extends, the bore being sized to contain a medical element and including an opening formed at a distal end of the body;
    a fin connected to the body in proximity to the distal end thereof, the fin comprising a terminal end, located proximal to the distal end of the body, and a relatively flat distal-facing surface that extends proximally from the opening of the bore to the terminal end of the fin at an acute angle with respect to a longitudinal axis of the bore; and
    an injection rod including a distal surface, the injection rod fitting within the bore and moveable along the longitudinal axis to a position in relatively close proximity to the opening of the bore where the distal surface of the injection rod is approximately coplanar with the distal-facing surface of the fin.

2. The tool of claim 1, wherein the body includes a retention feature for temporarily holding one of: the injection rod and the medical element within the bore.

3. The tool of claim 2, wherein the body further includes another retention feature for temporarily holding the other of the injection rod and the medical element within the bore.

4. The tool of claim 3, wherein the retention feature, which holds the injection rod, holds the injection rod at an initial position where the distal facing surface of the rod is located at a distance from the position in relatively close proximity to the opening of the bore, the distance accommodating the medical element, when contained within the bore.

5. The tool of claim 1, wherein the distal end of the body comprises an expandable portion that defines the opening of the bore when expanded.

6. The tool of claim 1, wherein the distal end of the body is enlarged from an adjacent section of the body.

7. The tool of claim 1, wherein the acute angle, at which the flat distal-facing surface of the fin extends, is no greater than approximately 60 degrees.

8. The tool of claim 1, wherein the injection rod further includes a lumen extending from a proximal end thereof to an opening in proximity to the distal surface of the rod.

9. The tool of claim 1, wherein the fin tapers inward across a width of the distal-facing surface and toward the terminal end.

10. A medical system comprising a medical element and a transcutaneous implant tool, the implant tool comprising:
an elongate body comprising a bore and having a length along which the bore extends, the bore containing the medical element and including an opening formed at a distal end of the body;
a fin connected to the body in proximity to the distal end thereof, the fin comprising a terminal end, located proximal to the distal end of the body, and a relatively flat distal-facing surface that extends proximally from the opening of the bore to the terminal end of the fin at an acute angle with respect to a longitudinal axis of the bore; and
an injection rod including a distal surface, the injection rod fitting within the bore and moveable along the longitudinal axis to a position in relatively close proximity to the opening of the bore where the distal surface of the injection rod is approximately coplanar with the distal-facing surface of the fin;
wherein the medical element is wholly contained within the bore of the body, before the injection rod is moved to the position in relatively close proximity to the opening of the bore.

11. The system of claim 10, wherein the body of the implant tool includes a retention feature for temporarily holding one of the injection rod of the implant tool and the medical element within the bore of the tool.

12. The system of claim 11, wherein the body of the implant tool further includes another retention feature for temporarily holding the other of the injection rod of the implant tool and the medical element within the bore.

13. The system of claim 12, wherein the retention feature of the implant tool, which holds the injection rod, holds the injection rod at an initial position where the distal facing surface of the rod is located at a distance from the position in relatively close proximity to the opening of the bore of the implant tool, the distance being between approximately 4 cm and approximately 6 cm.

14. The system of claim 10, where a perimeter profile of the bore approximately matches that of the medical element.

15. The system of claim 10, wherein the medical element comprises a device having at least one sensor.

16. The system of claim 10, wherein the distal end of the body of the implant tool comprises an expandable portion that defines the opening of the bore of the body when expanded.

17. The system of claim 10, wherein the distal end of the body of the implant tool is enlarged from an adjacent section of the body.

18. The system of claim 10, wherein the acute angle, at which the flat distal-facing surface of the fin of the implant tool extends, is no greater than approximately 60 degrees.

19. The system of claim 10, wherein the injection rod of the implant tool further includes a lumen extending from a proximal end thereof to an opening in proximity to the distal surface of the rod.

20. The system of claim 10, wherein the fin of the implant tool tapers inward across a width of the distal-facing surface and toward the terminal end.

21. A transcutaneous implant tool comprising:
an elongate body defining a bore and having a length along which the bore extends, the bore being sized to contain a medical element and including an opening formed at a distal end of the body;
a fin connected to the body in proximity to the distal end thereof, the fin comprising a terminal end, located proximal to the distal end of the body, and a relatively flat distal-facing surface that extends proximally from the opening of the bore to the terminal end of the fin at an acute angle with respect to a longitudinal axis of the bore; and
an injection rod including a distal surface, the injection rod fitting within the bore and moveable along the longitudinal axis to a position in relatively close proximity to the opening of the bore where the distal surface of the injection rod is approximately coplanar with the distal-facing surface of the fin; and wherein:
the body further comprises a proximal section and a distal section, the bore extending through the distal section, and the proximal section extending laterally away from the longitudinal axis and proximally from the distal section to a proximal end of the body;
the injection rod includes a lateral projection extending from a proximal end of the injection rod, the proximal end of the injection rod being located outside the bore, when the rod is fitted within the bore; and
the lateral projection of the injection rod abuts the proximal end of the body when the injection rod is moved past the position in relatively close proximity to the opening of the bore.

22. A medical system comprising a medical element and a transcutaneous implant tool, the implant tool comprising:
an elongate body comprising a bore and having a length along which the bore extends, the bore containing the medical element and including an opening formed at a distal end of the body;
a fin connected to the body in proximity to the distal end thereof, the fin comprising a terminal end, located proximal to the distal end of the body, and a relatively flat distal-facing surface that extends proximally from the opening of the bore to the terminal end of the fin at an acute angle with respect to a longitudinal axis of the bore: and
an injection rod including a distal surface, the injection rod fitting within the bore and moveable along the longitudinal axis to a position in relatively close proximity to the opening of the bore where the distal surface of the injection rod is approximately coplanar with the distal-facing surface of the fin;
wherein the medical element is wholly contained within the bore of the body, before the injection rod is moved to the position in relatively close proximity to the opening of the bore: and wherein:
the body of the implant tool further comprises a proximal section and a distal section, the bore extending through the distal section, and the proximal section extending laterally away from the longitudinal axis and proximally from the distal section to a proximal end of the body;
the injection rod of the implant tool includes a lateral projection extending from a proximal end of the injection rod, the proximal end of the injection rod being located outside the bore of the implant tool, when the rod is fitted within the bore; and
the lateral projection of the injection rod abuts the proximal end of the body of the implant tool, when the injection rod is moved past the position in relatively close proximity to the opening of the bore.

* * * * *